United States Patent [19]

Kessler

[11] 4,120,770

[45] Oct. 17, 1978

[54] APPARATUS FOR THE POLAROGRAPHIC MEASUREMENT OF OXYGEN

[75] Inventor: Manfred Kessler, Dortmund, Fed. Rep. of Germany

[73] Assignee: Max-Planck-Gesellschaft zur Förderung der Wissenschaften e.V., Gottingen, Fed. Rep. of Germany

[21] Appl. No.: 817,663

[22] Filed: Jul. 21, 1977

[30] Foreign Application Priority Data

Jul. 22, 1976 [DE] Fed. Rep. of Germany ....... 2632931

[51] Int. Cl.² ............................................. G01N 27/54
[52] U.S. Cl. ................................ 204/195 R; 128/2 E; 204/1 T; 204/195 B; 324/29
[58] Field of Search ................... 204/1 Y, 1 P, 195 B, 204/195 R, 195 P; 128/2 E, 2 G, 2.1 E; 324/29

[56] References Cited

U.S. PATENT DOCUMENTS 3,918,434 11/1975 Lubbers .............................. 128/2 E Primary Examiner—G. L. Kaplan
Attorney, Agent, or Firm—Michael J. Striker

[57] ABSTRACT

The oxygen concentration (partial pressure) in a perfused medium, such as human tissue through which blood is perfused, is measured polarographically. The polarographic measurement process itself consumes oxygen, and tends to yield a read-out lower than the true concentration. Non-zero perfusion tends to replenish the consumed oxygen, thus counteracting the too low read-out, but the read-out is still lower than the true concentration. The uncorrected oxygen measurement is corrected by one factor to simulate a condition wherein perfusion is zero but oxygen consumption is non-zero, and by a second factor to simulate a condition in which the perfusion has its actual value but oxygen consumption is zero, thereby yielding an accurate oxygen read-out. A switchover device connects a polarography electrode and a reference electrode across a hydrogen-generating unit, and then a polarograhic hydrogen-measuring unit, and then a polarographic oxygen-measuring unit, in succession. The information concerning the wash-out of the generated hydrogen is converted into a corrective factor compensating for the non-zero perfusion. The other corrective factor is introduced to compensate for the effect of the non-zero perfusion upon the rate at which oxygen is consumed during the polarographic measurement, by taking into account the diffusion resistance of the type of tissue involved.

6 Claims, 2 Drawing Figures

APPARATUS FOR THE POLAROGRAPHIC MEASUREMENT OF OXYGEN

BACKGROUND OF THE INVENTION

The invention relates to polarographic measurement of oxygen concentration, performed using a polarography electrode and a reference electrode.

If oxygen is physically or chemically bound to a substance, there sets in an equilibrium as between free and bound oxygen. Polarographic oxygen-concentration measurements are most easily and accurately performed when this equilibrium is in existence. If this equilibrium becomes disturbed, it thereafter tends to become reestablished, by means of diffusion. For example, if the partial pressure of oxygen is to be ascertained by polarographic determination of free oxygen, then the oxygen which is consumed by the polarographic measuring procedure itself must be replenished, e.g. continually replenished, by means of diffusion. However, due to the low speed at which the replenishment by diffusion proceeds, the replenishment is not complete. As a result, a concentration gradient develops within the medium being analyzed, and there is simulated a value of the oxygen partial pressure which is lower than the actual value of the partial pressure.

A variety of techniques are known for overcoming this difficulty. One technique involves setting the medium to be analyzed into convective motion during the course of the polarographic measurement; this speeds the rate at which oxygen consumed by the measurement process itself can be replenished from portions of the medium not most directly involved in the electrolytic current path. Another known technique involves the use of electrodes whose effective surfaces are extremely small; this makes the electrolytic current path through the medium being analyzed so "thin" that oxygen consumed within this zone is very quickly replenished by diffusion from the medium surrounding this "thin" depletion zone, so quickly that equilibrium is maintained substantially uninterruptedly with substantially no development of the aforementioned concentration gradient. Finally, because the correlation between the shape and characteristics of these diffusion fields, on the one hand, and the shape and effective surface area of the electrodes used, on the other hand, is well understood in the art, it is also known to take this correlation expressly into account for the particular electrodes employed, and to correct the too low value of oxygen partial pressure simulated during the polarographic measurement, by introducing corresponding correction factors (GRUNEWALD, Diss. Marburg 1966).

However, these prior-art techniques are not applicable, when one is faced with the still further complications which arise when the oxygen whose concentration is to be measured is carried within media undergoing highly fluctuating perfusion, for example the oxygen in tissues through which blood is perfused.

In such cases, i.e., when the measuring electrodes are introduced into the capillary system, even empirically and/or theoretically devised models such as referred to above are inadequate for the development of correction factors, and so the actual magnitude of the oxygen partial pressure in the tissue cannot be ascertained with any directness.

Inasmuch as the case described above is very important, i.e., is the typical example of polarography applied to physiological measurements, certain techniques have been devised to permit oxygen concentration measurement, even in these circumstances. It is known to simultaneously determine the perfusion and the oxygen partial pressure, and then based on that information to calculate the perfusion efficiency. Then, if the rate at which oxygen is consumed by the polarographic apparatus is kept small, i.e., by maintaining the effective surface area of the electrodes small in the way described above, and if the perfusion is measured for example using the heat-flow procedure of HENSEL, it becomes possible to reliably ascertain the value of oxygen partial pressure, e.g., transcutaneously, and this value will correspond to the local arterial oxygen partial pressure in the capillary system (see German allowed patent application DT-AS No. 22 55 879 or corresponding U.S. Pat. No. 3,918,434).

However, a disadvantage of the aforementioned technique is that the electrodes employed must have an effective surface area of only a few square microns, to keep the oxygen consumption low. Electrodes having so minute an effective surface area are not dimensionally reliable except for relatively short periods of use. On the other hand, if electrodes are used having an effective surface area of more than 100 square microns, then the long-term dimensional reliability of the electrodes is certainly satisfactory; but then the aforedescribed errors attributable to the slowness at which oxygen is replenished by diffusion processes, are again no longer tolerable. An additional disadvantage of this known technique is that the consolidation of a polarographic probe and a thermo probe into a single component makes for a component which is very complex mechanically and highly malfunction-prone.

Still another way of dealing with the difficulty presented by the sluggishness of diffusion processes resides in the use of pulse techniques (Pflügers Arch. 276/pp. 415 ff.). In these techniques, the electrodes employed can be of comparatively large effective surface area. However, the oxygen partial pressure in the tissue of interest is not detected directly. Instead, what is measured is the oxygen partial pressure in a special chamber arranged intermediate the tissue of interest and the measuring electrodes. The oxygen partial pressure within this special chamber must be maintained in equilibrium with that in the tissue itself. The contents of the measuring chamber are exhausted during the course of the polarographic measurement. To generate an accurate measurement with this apparatus, it is critical that the dimensions of the measuring chamber be very precisely correlated with the effective surface area of the electrodes and with the length of the time interval during which the polarographic measurement is performed. The technical complexities of this method are very considerable, and it has not achieved widespread use.

Finally, it is also known to measure perfusion using the hydrogen-clearance technique (Pflügers Arch. 348/225). With this technique, a pair of electrodes is first used to generate hydrogen within the perfused medium to be analyzed. The generated hydrogen is then washed out by the perfusion flow itself. If one polarographically measures the hydrogen partial pressure, then by knowing the drop in the hydrogen partial pressure attributable to this wash-out, information can be derived concerning the actual perfusion rate.

SUMMARY OF THE INVENTION

It is a general object of the invention to provide a novel polarographic measuring technique for ascertaining oxygen partial pressure, using electrodes exhibiting good long-term dimensional reliability and an apparatus which is relatively simple to manufacture and use.

According to one concept of the invention, this is achieved using a switchover device. The switchover device electrically connects the measuring electrodes, in succession, to a voltage source to effect $H_2$ generation, then to a polarographic measuring and indicating device for measuring the $H_2$ partial pressure, and then to a polarographic measuring and indicating device for measuring the $O_2$ partial pressure.

With this technique, it becomes possible to measure the oxygen partial pressure with sufficient accuracy, using electrodes whose effective surface area is relatively large and dimensionally stable. The component of the measured value of oxygen concentration attributable to perfusion is determinable; and the pressure drop attributable exclusively to diffusion resistance, in contrast, is constant and can be ascertained using empirical and/or theoretical models.

According to a further concept of the invention, the measurement signal for the $H_2$ partial pressure is utilized as a correction signal and is applied to an adjustable corrective stage in the indicator arrangement for the $O_2$ partial pressure. Thus, it becomes possible to achieve a direct read-out of oxygen partial pressure which is independent of variations in the perfusion rate through the tissue of interest, and therefore independent of the corresponding variations in the rate of oxygen consumption.

According to another concept of the invention, use is made of a further corrective stage, settable to correct for the diffusion resistance within the type of tissue involved. With this further correction, it becomes possible to calibrate the oxygen partial pressure read-out absolutely.

It is advantageous that the aforementioned switchover device be switched over automatically and periodically. This makes the inventive apparatus suitable for monitoring purposes, e.g., in intensive-care units and during the course of surgical procedures.

It has been found that sufficiently accurate oxygen partial-pressure read-outs are achieved if the duration of each one of the successive phases ($H_2$ generation, $H_2$ measurement, $O_2$ measurement) is between about 20 seconds and about 3 minutes; i.e., the switchover device is preferably switched over automatically at time intervals of this length.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
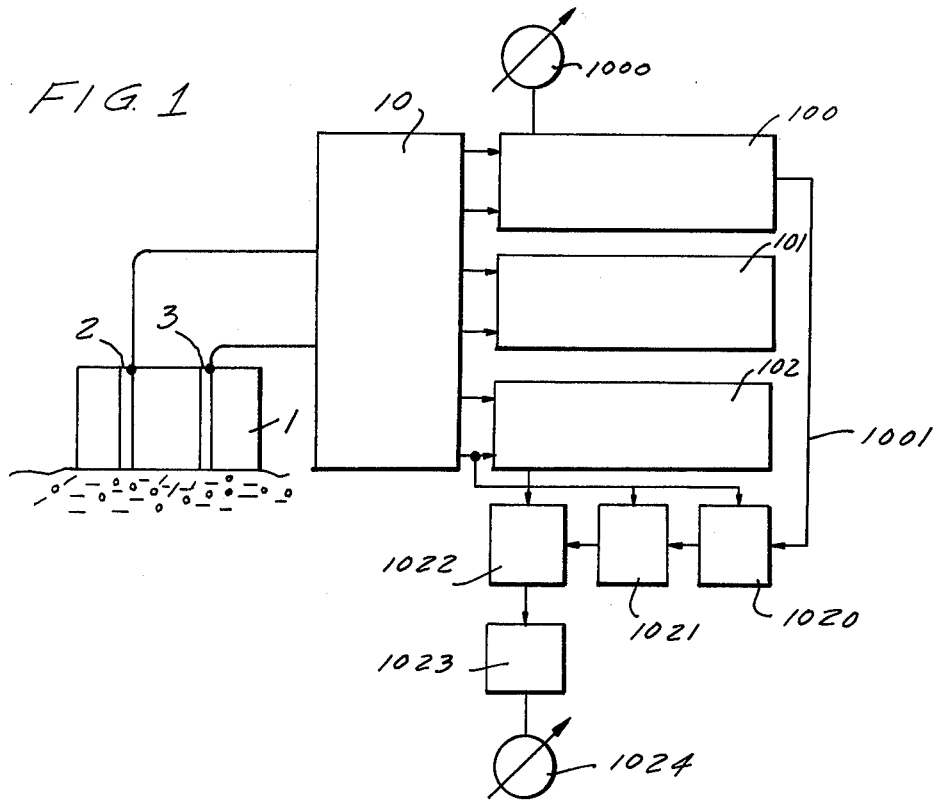
FIG. 1 schematically depicts an exemplary embodiment of the inventive apparatus.

In the apparatus schematically depicted in FIG. 1, a measuring probe 1 is provided with a polarography electrode 2 having a diameter of about 100 microns, or more, and a reference electrode 3. A switchover device 10 successively connects the two electrodes 2, 3 across the two output terminals of a voltage source 101, then across the two terminals of a polarographic measuring and indicating unit 100, 1000 for hydrogen concentration, and then across the two terminals of a polarographic measuring and indicating unit 102, 1024 for oxygen concentration — i.e., in the stated order.

The output signal from unit 100, indicative of hydrogen partial pressure, is applied via a line 1001 to the input of an integrator 1020. The signal at the output of integrator 1020 is applied to the input of an electronic switch 1021. The electronic switch 1021, when conductive, transmits this signal to the correction-signal input of a first correction unit 1022. The other, or main input of the first correction unit 1022 receives the output signal from unit 102, indicative of oxygen partial pressure. The output signal of first correction unit 1022, as explained below, has a value corresponding to the value of the oxygen-partial-pressure signal from unit 102 multiplied (or equivalently, divided) by the value of a correction signal derived from integrator 1020. The output signal from first correction unit 1022 (the oxygen-partial-pressure signal with the inclusion of the first correction factor) is applied to an oxygen-partial-pressure indicator 1024, through the intermediary of a second correction unit 1023. Second correction unit 1023 is manually adjustable, and multiplies the once corrected oxygen-partial-pressure signal from unit 1022 by a second correction factor, which is selected in advance to take into account the diffusion resistance of the type of tissue involved; this is explained below.

Switchover device 10 additionally has an output (conveniently constituted, for example, by its connection to unit 102) connected to the control input of electronic switch 1021 for rendering the latter conductive and non-conductive, and also connected to the control input of integrator 1020 for initiating and/or terminating the integration operation and/or for resetting the intergrator.

The sequence of operation of the illustrated embodiment is explained as follows, with respect to the signal diagrams shown in FIG. 2:

At time $t_i$, the switchover device 10 connects the two electrodes 2, 3 across the output terminals of voltage source 101. The latter applies across the electrodes 2, 3 a voltage of between about 500 and 1200 millivolts, effecting the generation of hydrogen within the medium of interest. As the concentration of thusly generated hydrogen increases, the interelectrode current I (101) builds up, during the time interval from $t_i$ to $t_{i+1}$, to a steady value of between 0.001 to 1 microamperes, after which it remains constant at this value, during the time interval from $t_{i+1}$ to $t_{i+2}$.

Some time after this steady value of current has been reached at time $t_{i+1}$, and in the illustrated example at the moment $t_{i+2}$, the generation of hydrogen is interrupted. I.e., at moment $t_{i+2}$, the switchover device 10 disconnects the electrodes 2, 3 from voltage source 101, and now connects them across the two terminals of polarographic hydrogen measuring and indicating unit 100, 1000.

During the interval from $t_{i+2}$ to $t_{i+3}$, the thusly-generated hydrogen is washed out by the perfusion of blood through the tissue of interest. Accordingly, the output signal P(100) of polarographic hydrogen measuring unit 100, which is proportional to the hydrogen concentration, decreases correspondingly, as shown in FIG. 2 for the time interval from $t_{i+2}$ to $t_{i+3}$.

Starting from the moment $t_{i+2}$, at which unit 100 begins to furnish its hydrogen-concentration output signal P(100), this signal P(100) is applied via line 1001 to the input of integrator 1020. Integrator 1020 accordingly generates, during the time interval between $t_{i+2}$ and $t_{i+3}$, the time-integral signal of P(100).

At moment $t_{i+3}$, the switchover device 10 disconnects the two electrodes 2, 3 from the hydrogen-measuring unit 100 and now connects the two electrodes across the terminals of the oxygen-measuring unit 102. The oxygen-measuring unit 102 furnishes at its output an oxygen-concentration signal P(102), as shown in FIG. 2. This signal P(102) is applied to the main input of first correction unit 1022. The other input of correction unit 1022 receives, during the time interval from $t_{i+3}$ to $t_{i+4}$, the time-integral information from integrator 1020; i.e., the electronic switch 1021 is rendered conductive by the switchover device 10 at time $t_{i+3}$ and kept conductive until time $t_{i+4}$.

As a result, during the time interval from $t_{i+3}$ to $t_{i+4}$, the corrected oxygen-concentration signal appearing at the output of correction unit 1022 is equal to P(102) . $K_2(f)$, wherein $K_2(f)$ is equal to $$\frac{P_o}{\int_{t_{i+2}}^{t_{i+3}} P(100)\, dt}$$

In the above expression, $P_o$ is the value of P(100) at the moment $t_{i+2}$, i.e., at the start of the hydrogen washout; $f$ is the perfusion rate.

The formation of the output signal P(102) . $K_2(f)$ at the output of correction unit 1022 can be performed in various ways:

Unit 1022 can be a divider, operative for dividing the signal from unit 102 by the signal from unit 1020; in that case, integrator 1020 can be a simple integrator and its output signal can be equal to the aforedefined time integral of P(100), with the inclusion of $P_o$ in the form of a proportionality constant. Alternatively, the value $P_o$ can be positively ascertained at moment $t_{i+2}$, by means of a sample-and-hold stage within integrator unit 1020, stored (held) throughout the time interval from $t_{i+3}$ to $t_{i+4}$, with this stored value being included, in the form of a proportionality factor, in the output signal of integrator unit 1020. If the value $P_o$ is not positively ascertained in this way, but instead has the form of a constant proportionality factor, then it could alternatively be introduced within correction unit 1022.

Instead of being a divider, unit 1022 can be a multiplier, operative for multiplying the signal from unit 102 by the signal from unit 1020. In that case, to form the correction signal $K_2(f)$ at the output of integrator unit 1020, the latter should include a divider, i.e. to form the reciprocal of the time integral of P(100). Again, the proportionality factor $P_o$, if it is a constant proportionality factor, can be introduced either within the integrator unit 1022 or within the multiplier 1022; and if the factor $P_o$ is generated by means of a sample-and-hold stage (as mentioned above), then the sample-and-hold stage would be included in integrator unit 1020.

In any event, the important consideration is that the signal at the output of first correction unit 1022 be equal to P(102) . $K_2(f)$ as defined above.

The divider or multiplier 1022 can be of any conventional type, e.g. such as conventional in analog computer circuits, or can be electromechanical such as a voltage divider across which the signal P(102) is applied with the tap of the voltate divider being adjusted by an adjuster motor energized by the signal from integrator unit 1020; or can be a self-regulating compensation potentiometer, etc.

The output signal from first correction unit 1022 is applied to the input of the second correction unit 1023. Unit 1023 is manually adjustable, and the technician selects the setting of unit 1023 in dependence upon the type of tissue involved, the required setting being taken from an empirically developed tabulation of tissue types and required settings. Second correction unit 1023 is operative for applying to the output signal from unit 1022 a further correction factor, corresponding to the diffusion resistance of the type 1 of tissue involved. The empirically developed tabulation of the corresponding compensatory proportionality factors $1_k$, once established will always be ready on hand, for use in setting unit 1023.

The development of the empirical tabulation of the setting for unit 1023 is not difficult to perform. For each different tissue type to be included in the tabulation, the operation described above is performed (i.e., a complete measuring cycle from $t_i$ to $t_{i+4}$), but with the perfusion of blood through the tissue maintained at zero and 100% oxygenation of the blood. For each tissue type, the setting of unit 1023 is adjusted, on a trial and error basis, to a respective setting such that the output signal $P_3$ of unit 1023 is the same for all tissue types. Thus, each setting $1_k$ of unit 1023 will, as a result, be established in accordance with the following equation:

$$l_K = \frac{P_3}{P(102) \cdot K_2(f)}$$

These values of $1_k$ are then tabulated, alongside the respective tissue types.

Accordingly, after this one-time tabulation, each time the apparatus is to be used for a particular tissue type, the setting of unit 1023, determined from the tabulation, will be such that $$P_3 = 1_k \cdot P(102) \cdot K_2(f).$$

Figure 2:
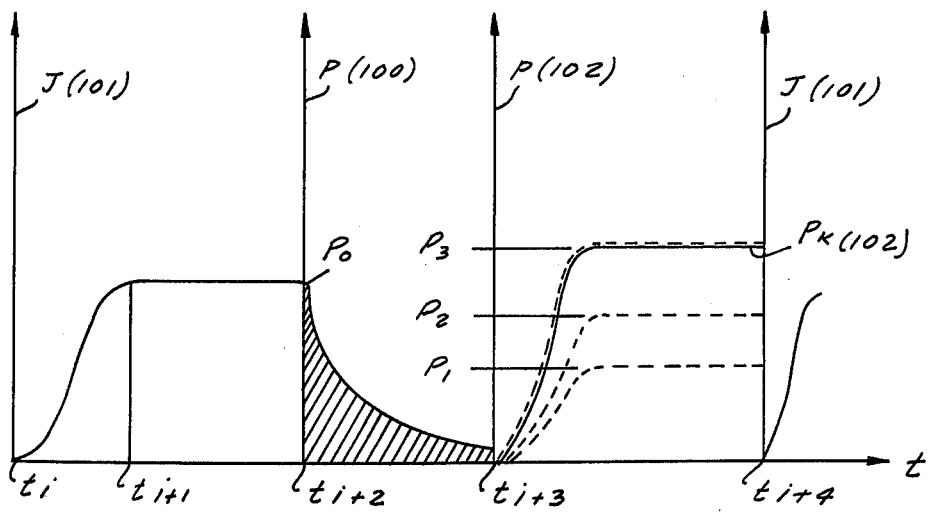
FIG. 2 depicts signal waveformss which are referred to in the explanation of the operation of the apparatus of FIG. 1.

The meaning of the application of these two corrective factors (i.e., in the two correction stages 1022, 1023) will be understood with reference to the time interval $t_{i+3}$ to $t_{i+4}$ in FIG. 2. At the switchover moment $t_{i+3}$, when the electrodes 2, 3 become operatively connected to the oxygen-measuring unit 102, the output signal P(102) of the latter initially rises and then assumes a steady value. In FIG. 2, the value $P_2$ is the value assumed by the completely uncorrected oxygen-concentration signal at the output of oxygen measuring unit 102 — i.e., the value of this signal is affected by the fact that the polarographic measurement process itself consumes oxygen and therefore yields a lower than true value, even if the measurement were performed at zero perfusion. Additionally, the value of this signal is affected by the fact that the measurement is performed at non-zero perfusion, as a result of which consumed oxygen is more quickly replenished during the measurement operation, yielding an oxygen concentration value which is higher than if the measurement were performed at zero perfusion, but nevertheless lower than the true oxygen concentration value (i.e., lower than if the measurement could be performed in the perfused medium but with zero oxygen consumption).

The value $P_1$ shown in FIG. 2 is the value which oxygen-concentration signal P(102) would have assumed in the case of zero perfusion, but with non-zero oxygen consumption by the electrode.

The value $P_3$ shown in FIG. 2 is the value which the output signal of unit 1022 actually assumes and is indicative of the oxygen concentration at the prevailing perfusion rate, with the effect of oxygen consumption eliminated — i.e., as though the polarographic process did not itself consume oxygen.

The corrective proportionality factor introduced by correction unit 1023 compensates for the oxygen difference $P_2-P_1$ attributable to the non-zero perfusion rate. In other words, if only this corrective factor were introduced, then the output signal applied to indicator 1024 would have the value $P_1$, and would simulate the situation where perfusion is zero.

In contrast, the corrective proportionality factor introduced by unit 1022 compensates for the oxygen discrepancy $P_3-P_2$.

It will be noted that the value $P_2$ is the value assumed by the completely uncorrected output signal from oxygen-measuring unit 102. Value $P_3$ is the value which ideally should be assumed, and with the present invention actually is assumed. Value $P_1$ is of no interest in itself; but it is not possible to apply a single corrective factor which would convert the value $P_2$ to the value $P_3$ directly. Instead, in effect, the value $P_2$ must be converted to the value $P_1$, and then the value $P_1$ can be converted into the accurate oxygen-concentration value $P_3$, i.e., thus involving two corrective factors used simultaneously.

Preferably, the switchover device switches from one phase of the measuring cycle to the next automatically and cyclically at time intervals whose duration is between 20 seconds and 3 minutes.

It will be understood that the polarographic measuring units 100 and 102, themselves, are conventional in the art. These can be, merely by way of example, of the types disclosed in German published patent application DT-OS No. 2,255,879, or in the published article "Die Messung des absoluten Sauerstoffdruckes mit der Kammer-Pt-Elektrode in beliebigen Medien, insbesondere im Blut und Gewebe", by K. Kunze, D. W. Lubbers and E. Windisch, submitted on Aug. 1, 1962 to the Ausserordentlicher Lehrstuhl fur angewandte Physiologie und Arbeitsphysiologie der Universitat Marburg/Lahn; however, polarographic measuring units are conventional in the art, in general, and as used in the present invention do not require special modifications or set-up.

It will be understood that each of the elements described above, or two or more together, may also find a useful application in other types of circuits and constructions differing from the types described above.

While the invention has been illustrated and described as embodied in an apparatus for measuring oxygen concentration in tissue through which blood is perfused, it is not intended to be limited to the details shown, since various modifications and structural changes may be made without departing in any way from the spirit of the present invention.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An apparatus for the polarographic measurement of oxygen concentration comprising, in combination, a polarography electrode and a reference electrode for engagement with the medium to be analyzed, the polarography electrode having an effective diameter of 100 microns or more; first means operative when connected across the electrodes for effecting hydrogen generation within the medium and including a voltage source; second means operative when connected across the electrodes for effecting a polarographic measurement of hydrogen concentration; third means operative when connected across the electrodes for effecting a polarographic measurement of oxygen concentration; and switchover means operable for connecting the first, second and third means, in succession, across the electrodes.

2. The apparatus defined in claim 1, further comprising first corrective means operative for automatically correcting the measurement performed by the third means in dependence upon the measurement performed by the second means.

3. The apparatus defined in claim 2, further comprising second corrective means operative for correcting the measurement performed by the third means in dependence upon the diffusion resistance of the medium.

4. The apparatus defined in claim 1, the switchover means comprising means operative for automatically and cyclically connecting the first, second and third means, in succession, across the electrodes.

5. The apparatus defined in claim 4, the switchover means connecting each of the first, second and third means across the electrodes for a respective time interval whose duration is between 20 seconds and 3 minutes.

6. The apparatus defined in claim 1, further comprising first corrective means operative for automatically correcting the measurement performed by the third means by deriving from the measurement performed by the second means information indicative of the perfusion rate of the medium.

* * * * *